US009328070B2

(12) United States Patent
Jaeschke et al.

(10) Patent No.: US 9,328,070 B2
(45) Date of Patent: May 3, 2016

(54) ETHYNYL DERIVATIVES

(71) Applicant: Hoffmann-La Roche Inc., Little Falls, NJ (US)

(72) Inventors: Georg Jaeschke, Basel (CH); Lothar Lindemann, Basel (CH); Antonio Ricci, Birsfelden (CH); Daniel Rueher, Raedersdorf (FR); Heinz Stadler, Basel (CH); Eric Vieira, Frenkendorf (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/689,366

(22) Filed: Apr. 17, 2015

(65) Prior Publication Data

US 2015/0225344 A1    Aug. 13, 2015

Related U.S. Application Data

(63) Continuation of application No. PCT/EP2013/071493, filed on Oct. 15, 2013.

(30) Foreign Application Priority Data

Oct. 18, 2012    (EP) ..................................... 12189015

(51) Int. Cl.
*C07D 213/81*  (2006.01)
(52) U.S. Cl.
CPC ................................... *C07D 213/81* (2013.01)

(58) Field of Classification Search
CPC ...................................................... C07D 213/81
USPC ........................................... 546/323; 514/354
See application file for complete search history.

(56) References Cited

U.S. PATENT DOCUMENTS 8,772,300 B2 *    7/2014    Jaeschke .............. C07D 213/56
                                                514/256

* cited by examiner

*Primary Examiner* — Patricia L Morris
(74) *Attorney, Agent, or Firm* — Tamara A. Kale

(57) ABSTRACT

The present invention relates to ethynyl derivatives of formula I

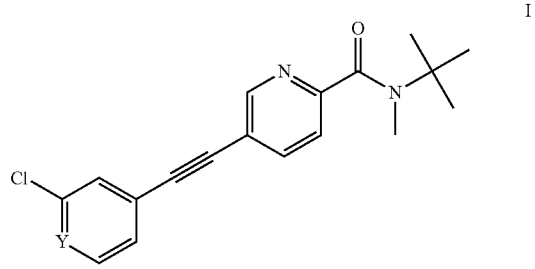

wherein
Y is N or CH
or to a pharmaceutically acceptable acid addition salt, to a racemic mixture, or to its corresponding enantiomer and/or optical isomer and/or stereoisomer thereof.

2 Claims, 1 Drawing Sheet

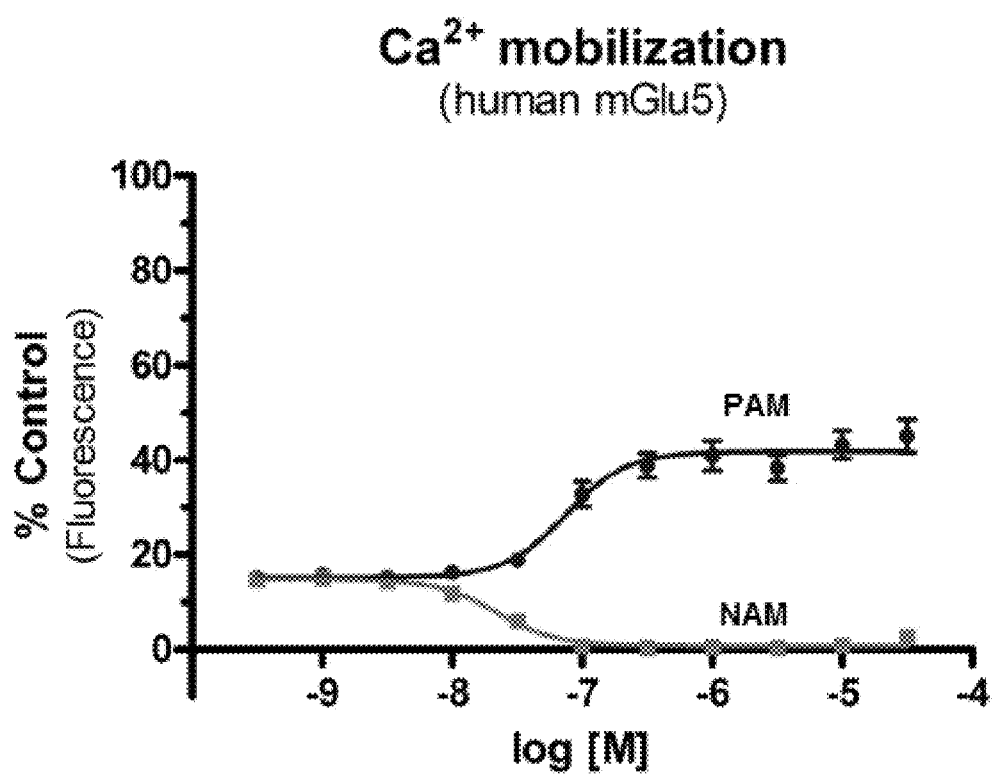

ETHYNYL DERIVATIVES

This application is a continuation of International Application PCT/EP2013/071493, filed Oct. 15, 2013, which claims the benefit of priority to European Application 12189015.6, filed Oct. 18, 2012, each of which is incorporated herein by reference in its entirety.

The present invention relates to ethynyl derivatives of formula I

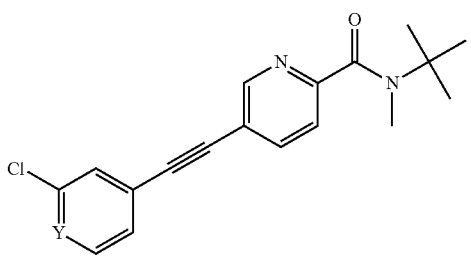

wherein

Y is N or CH or to a pharmaceutically acceptable acid addition salt, to a racemic mixture, or to its corresponding enantiomer and/or optical isomer and/or stereoisomer thereof.

It has now surprisingly been found that the compounds of general formula I are metabotropic glutamate receptor antagonists (NAM=negative allosteric modulators). Compounds of formula I are distinguished by having valuable therapeutic properties. They can be used in the treatment or prevention of mGluR5 receptor mediated disorders.

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Negative allosteric modulators of metabotropic glutamate receptors, belonging to the first group, can be used for the treatment or prevention of acute and/or chronic neurological disorders such as Parkinson's disease, Fragile-X syndrome, autistic disorders, cognitive disorders and memory deficits, as well as chronic and acute pain and gastroesophageal reflux disease (GERD).

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

Selective mGluR5 antagonists are especially useful for the treatment of disorders where reduction of mGluR5 receptor activation is desired, such as anxiety and pain, depression, Fragile-X syndrome, autism spectrum disorders, Parkinson's disease, and gastroesophageal reflux disease (GERD).

Objects of the present invention are compounds of formula I and their pharmaceutically acceptable salts, the above-mentioned compounds as pharmaceutically active substances and their production. Further objects of the invention are medicaments based on a compound in accordance with the invention and their manufacture as well as the use of the compounds in the control or prevention of mGluR5 receptor (NAM) mediated disorders, which are anxiety and pain, depression, Fragile-X syndrome, autism spectrum disorders, Parkinson's disease, and gastroesophageal reflux disease (GERD, and, respectively, for the production of corresponding medicaments.

One embodiment of the present invention are compounds of formula I, wherein Y is N.

This compound is 5-(2-chloro-pyridin-4-ylethynyl)-pyridine-2-carboxylic acid tert-butyl-methyl-amide.

One embodiment of the present invention are compounds of formula I, wherein Y is CH.

This compound is 5-(3-chloro-phenylethynyl)-pyridine-2-carboxylic acid tert-butyl-methyl-amide.

A particular embodiment of the invention consists of the following compounds: 5-(2-Chloro-pyridin-4-ylethynyl)-pyridine-2-carboxylic acid tert-butyl-methyl-amide 5-(3-Chloro-phenylethynyl)-pyridine-2-carboxylic acid tert-butyl-methyl-amide Compounds, which are similar to those of the present invention, have been generically described as positive allosteric modulators of the mGluR5 receptor. Surprisingly, it has been found that highly potent mGluR5 antagonists were obtained instead of mGluR5 positive allosteric modulators, which have a completely opposite pharmacology if compared with positive allosteric modulators.

The main difference between positive- and negative allosteric modulators can be seen in FIG. 1. A mGluR5 positive allosteric modulator (PAM) leads to increased receptor activity ($Ca^{2+}$ mobilisation) in presence of a fixed concentration of glutamate, whereas an allosteric antagonist (negative allosteric modulator, NAM) leads to a reduction of receptor activation. FIG. 1 shows the general behavior of a NAM and a PAM under the same conditions. The affinity for the receptor in FIG. 1 is ca. $10^{-7}$ M for the PAM and between $10^{-7}$ M and $10^{-8}$ M for the NAM. These values can also be measured using a binding assay to displace a radioligand (=MPEP), see assay description.

The indications which can be addressed by the compounds are not the same. mGluR5-NAMs are beneficial for indications where a reduction of excessive receptor activity is desired, such as anxiety and pain, depression, Fragile-X syndrome, autism spectrum disorders, Parkinson's disease, and gastroesophageal reflux disease (GERD). mGluR5 PAMs on the other hand are useful in indications where a normalization of decreased receptor activity is desired, such as in psychosis, epilepsy, schizophrenia, Alzheimer's disease and associated cognitive disorders, as well as tuberous sclerosis.

This difference can be practically shown for example in an anxiety animal model, such as in the "rat Vogel conflict drinking test", where the compounds of the invention show anxiolytic activity, whereas mGluR-PAMs do not show activity in this animal model.

BRIEF DESCRIPTION OF THE FIGURE

FIG. 1: Comparison of an mGluR5 positive allosteric modulator (PAM) and an mGluR5 antagonist (negative allosteric modulator=NAM).

BIOLOGICAL ASSAYS AND DATA

Intracellular $Ca^{2+}$ Mobilization Assay

A monoclonal HEK-293 cell line stably transfected with a cDNA encoding for the human mGlu5a receptor was generated; for the work with mGlu5 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 µg/ml hygromycin and 15 µg/ml blasticidin (all cell culture reagents and antibiotics from Invitrogen, Basel, Switzerland).

About 24 hrs before an experiment, $5 \times 10^4$ cells/well were seeded in poly-D-lysine coated, black/clear-bottomed 96-well plates. The cells were loaded with 2.5 µM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist L-glutamate was added to the cells at a concentration corresponding to $EC_{20}$ (typically around 80 µM) with on-line recording of fluorescence; in order to account for day-to-day variations in the responsiveness of cells, the $EC_{20}$ of glutamate was determined immediately ahead of each experiment by recording of a full dose-response curve of glutamate.

Responses were measured as peak increase in fluorescence minus basal (i.e. fluorescence without addition of L-glutamate), normalized to the maximal stimulatory effect obtained with saturating concentrations of L-glutamate. Graphs were plotted with the % maximal stimulatory using XLfit, a curve fitting program that iteratively plots the data using Levenburg Marquardt algorithm. The single site competition analysis equation used was $y=A+((B-A)/(1+((x/C)D)))$, where y is the % maximal stimulatory effect, A is the minimum y, B is the maximum y, C is the $EC_{50}$, x is the log 10 of the concentration of the competing compound and D is the slope of the curve (the Hill Coefficient). From these curves the $EC_{50}$ (concentration at which half maximal stimulation was achieved), the Hill coefficient as well as the maximal response in % of the maximal stimulatory effect obtained with saturating concentrations of L-glutamate were calculated.

Positive signals obtained during the pre-incubation with the PAM test compounds (i.e. before application of an $EC_{20}$ concentration of L-glutamate) were indicative of an agonistic activity, the absence of such signals were demonstrating the lack of agonistic activities. A depression of the signal observed after addition of the $EC_{20}$ concentration of L-glutamate was indicative of an inhibitory activity of the test compound.

In the list of examples below are shown the corresponding results for compounds, which all have $EC_{50}$ values less or equal 50 nM.

| Example | mGlu5 PAM $EC_{50}$ [nM] | Efficacy [%] |
| --- | --- | --- |
| Reference compound 1 | 16 | 64 |

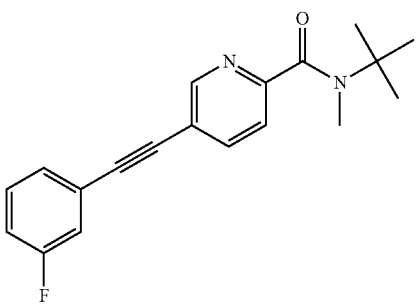

-continued

| Example | mGlu5 PAM EC$_{50}$ [nM] | Efficacy [%] |
|---|---|---|
| Reference compound 2 | 17 | 33 |
| Reference compound 3 | 37 | 80 |
| Ex. 1 | Inactive | |
| Ex. 2 | inactive | |

MPEP Binding Assay

For binding experiments, cDNA encoding human mGlu 5a receptor was transiently transfected into EBNA cells using a procedure described by Schlaeger and Christensen [Cytotechnology 15:1-13 (1998)]. Cell membrane homogenates were stored at −80° C. until the day of assay where upon they were thawed and resuspended and polytronised in 15 mM Tris-HCl, 120 mM NaCl, 100 mM KCl, 25 mM CaCl$_2$, 25 mM MgCl$_2$ binding buffer at pH 7.4 to a final assay concentration of 20 μg protein/well.

Saturation isotherms were determined by addition of twelve [$^3$H]MPEP concentrations (0.04-100 nM) to these membranes (in a total volume of 200 μl) for 1 h at 4° C. Competition experiments were performed with a fixed concentration of [$^3$H]MPEP (2 nM) and IC$_{50}$ values of test compounds evaluated using 11 concentrations (0.3-10,000 nM). Incubations were performed for 1 h at 4° C.

At the end of the incubation, membranes were filtered onto unifilter (96-well white microplate with bonded GF/C filter preincubated 1 h in 0.1% PEI in wash buffer, Packard BioScience, Meriden, Conn.) with a Filtermate 96 harvester (Packard BioScience) and washed 3 times with cold 50 mM Tris-HCl, pH 7.4 buffer. Nonspecific binding was measured in the presence of 10 μM MPEP. The radioactivity on the filter was counted (3 min) on a Packard Top-count microplate scintillation counter with quenching correction after addition of 45 μl of microscint 40 (Canberra Packard S.A., Zurich, Switzerland) and shaking for 20 min.

Comparison of Compounds of the Invention Versus the Reference Compounds 1 and 2

As can be seen in the table below, the compounds of the invention (NAM) show a clearly different profile compared to structurally similar reference compounds 1, 2 and 3 (PAM).

| Ex. | Structure | EC$_{50}$ (nM) mGlu5 PAM assay | Ki (nM) MPEP binding | Activity profile |
|---|---|---|---|---|
| Reference compound 1 | 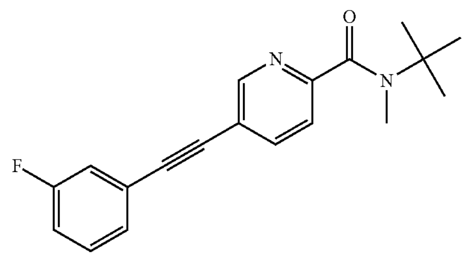 [SMILES: CN(C(=O)c1ccc(C#Cc2cccc(F)c2)cn1)C(C)(C)C] | 16 | 29 | PAM |
| Reference compound 2 | 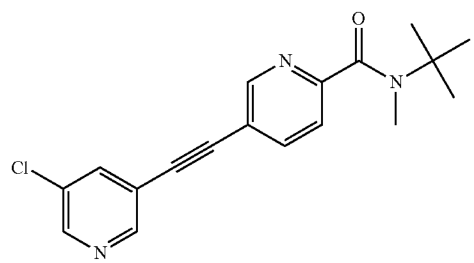 [SMILES: CN(C(=O)c1ccc(C#Cc2cncc(Cl)c2)cn1)C(C)(C)C] | 17 | 42 | PAM |
| Reference compound 3 | 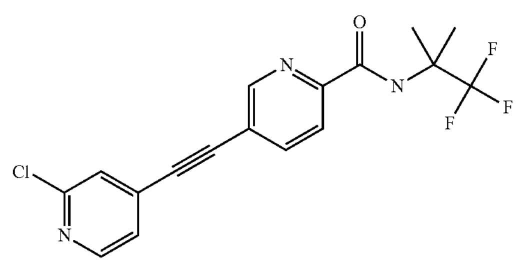 [SMILES: CC(C)(NC(=O)c1ccc(C#Cc2ccnc(Cl)c2)cn1)C(F)(F)F] | 37 | 58 | PAM |
| 1 | 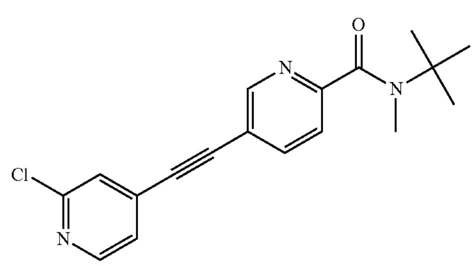 [SMILES: CN(C(=O)c1ccc(C#Cc2ccnc(Cl)c2)cn1)C(C)(C)C] | inactive | 28 | NAM |
| 2 | 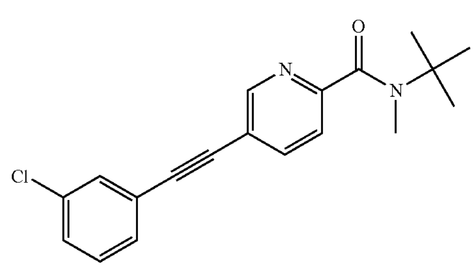 [SMILES: CN(C(=O)c1ccc(C#Cc2cccc(Cl)c2)cn1)C(C)(C)C] | inactive | 15 | NAM |

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts may be prepared by methods, known in the art, for example by the process variants described below, which process comprises a) reacting a compound of formula

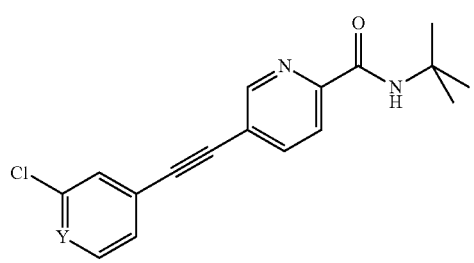

5 with the compound CH$_3$I
to a compound of formula

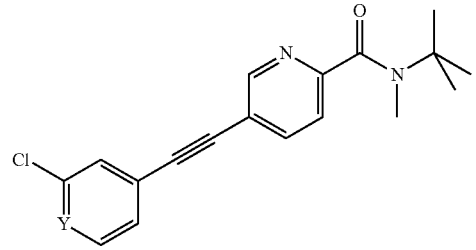

I wherein the substituents are described above, or b) reacting a compound of formula

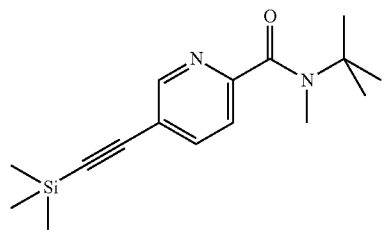

8 with a compound of formula

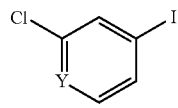

9 to a compound of formula

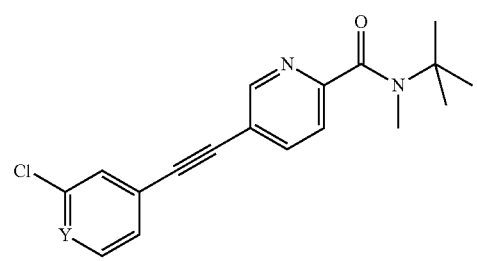

I wherein the substituents are described above.

The preparation of compounds of formula I is further described in more detail in schemes 1 & 2 and in examples 1-2.

Scheme 3

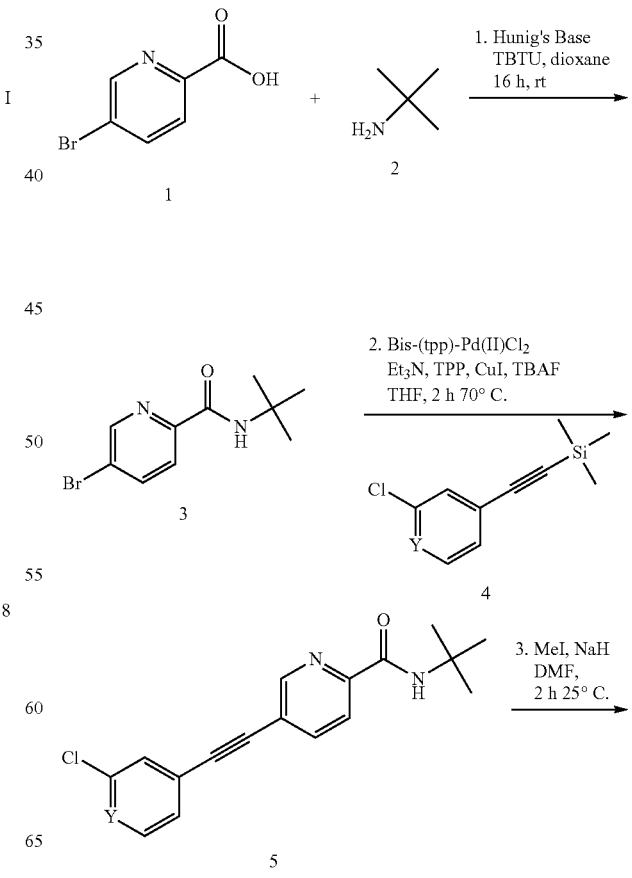

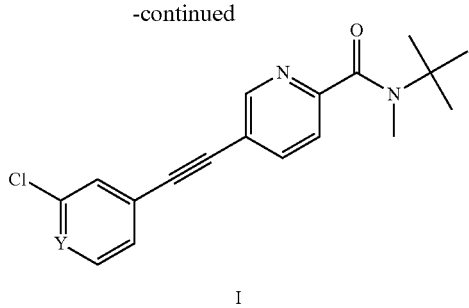

Example 1 can be obtained for example by reacting 5-bromo-pyridine-2-carboxylic acid 1 with tert. butyl amine 2 in presence of a base such as Hunig's Base and a peptide coupling reagent such as TBTU in a solvent such as dioxane. Sonogashira coupling of the 5-bromo-pyridine-2-carboxylic acid amide 3 with in-situ desilylation of the arylacetylene 4 yields the desired ethynyl compound 5. Alkylation of the ethynyl compound 5 with iodomethane and sodium hydride in a solvent such as DMF yields the desired Example 1 (scheme 1).

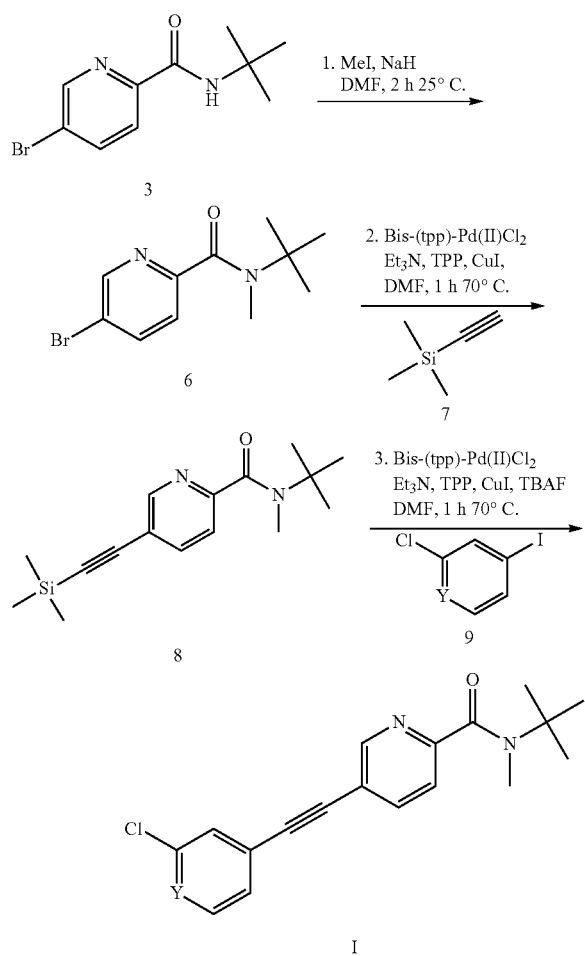

Example 2 can be obtained for example by alkylation of the 5-bromo-pyridine-2-carboxylic acid amide 3 with iodomethane and sodium hydride in a solvent such as DMF to yield the desired 5-bromo-pyridine-2-carboxylic acid amide 6. Sonogashira coupling of the 5-bromo-pyridine-2-carboxylic acid amide 6 with ethynyltrimethylsilane 7 yields the corresponding 5-trimethylsilanylethynyl-derivative 8. Sonogashira coupling with in-situ desilylation of 8 and 1-chloro-3-iodobenzene 9 yields the desired Example 2 (scheme 2).

Pharmaceutically acceptable salts of compounds of formula I can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

Moreover, the invention relates also medicaments containing one or more compounds of the present invention and pharmaceutically acceptable excipients for the treatment and prevention of mGluR5 receptor mediated disorders, such as anxiety and pain, depression, Fragile-X syndrome, autism spectrum disorders, Parkinson's disease, and gastroesophageal reflux disease (GERD).

The invention also relates to the use of a compound in accordance with the present invention as well as its pharmaceutically acceptable salt for the manufacture of medicaments for the treatment and prevention of mGluR5 receptor mediated disorders as outlined above.

Pharmaceutically acceptable salts of compounds of formula I can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

The pharmacological activity of the compounds was tested using the following method:

cDNA encoding rat mGlu 5a receptor was transiently transfected into EBNA cells using a procedure described by E.-J. Schlaeger and K. Christensen (*Cytotechnology* 1998, 15, 1-13). $[Ca^{2+}]i$ measurements were performed on mGlu 5a transfected EBNA cells after incubation of the cells with Fluo 3-AM (obtainable by FLUKA, 0.5 μM final concentration) for 1 hour at 37° C. followed by 4 washes with assay buffer (DMEM supplemented with Hank's salt and 20 mM HEPES. $[Ca^{2+}]i$ measurements were done using a fluorometric imaging plate reader (FLIPR, Molecular Devices Corporation, La Jolla, Calif., USA). When compounds were evaluated as antagonists they were tested against 10 μM glutamate as agonist.

The inhibition (antagonists) curves were fitted with a four parameter logistic equation giving $IC_{50}$, and Hill coefficient using the iterative non linear curve fitting software Origin (Microcal Software Inc., Northampton, Mass., USA).

The Ki values of the compounds tested are given. The Ki value is defined by the following formula:

$$K_i = \frac{IC_{50}}{1 + \frac{[L]}{EC_{50}}}$$

in which the $IC_{50}$ values are those concentrations of the compounds tested in µM by which 50% of the effect of compounds are antagonised. [L] is the concentration and the $EC_{50}$ value is the concentration of the compounds in µM which brings about 50% stimulation.

The compounds of the present invention are mGluR 5a receptor antagonists. The activities of compounds of formula I as measured in the assay described above are in the range of $K_i$<100 µM.

The compounds of formula I and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula I and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula I or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided to further elucidate the invention:

EXAMPLE 1

5-(2-Chloro-pyridin-4-ylethynyl)-pyridine-2-carboxylic acid tert-butyl-methyl-amide

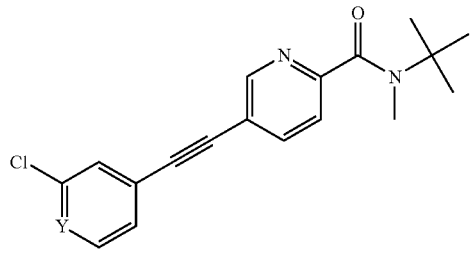

Step 1: 5-Bromo-pyridine-2-carboxylic acid tert-butylamide

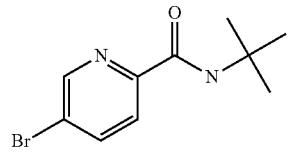

5-Bromopicolinic acid (200 mg, 0.99 mmol) was dissolved in dioxane (2 ml) and Hunig's Base (520 µl, 2.97 mmol, 3 equiv.), TBTU (350 mg, 1.09 mmol, 1.1 equiv.) and tert-butyl amine (124 µl, 1.19 mmol, 1.2 equiv.) were added at room temperature. The mixture was stirred for 16 hours at room temperature. The reaction mixture was evaporated and extracted saturated $NaHCO_3$ solution and two times with a small volume of dichloromethane. The crude product was purified by flash chromatography by directly loading the dichloromethane layers onto a silica gel column and eluting with an ethyl acetate:heptane gradient 0:100 to 50:50. The desired 5-bromo-pyridine-2-carboxylic acid tert-butylamide (235 mg, 92% yield) was obtained as a colorless oil, MS: m/e=257.0/259.0 (M+H$^+$).

Step 2: 5-(2-Chloro-pyridin-4-ylethynyl)-pyridine-2-carboxylic acid tert-butylamide

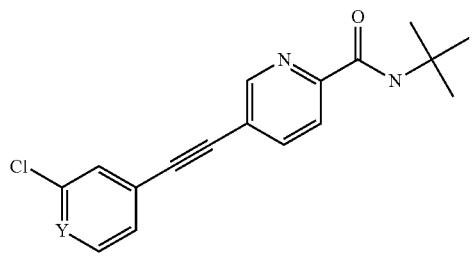

5-Bromo-pyridine-2-carboxylic acid tert-butylamide (Example 1, step 1) (280 mg, 0.92 mmol) was dissolved in THF (20 ml). 2-Chloro-4-trimethylsilanylethynyl-pyridine [CAS 499193-57-6] (222 mg, 1.06 mmol, 1.15 equiv.), Et$_3$N (1.28 ml, 9.2 mmol, 10 equiv.), Bis-(triphenylphosphine)-palladium(II)dichloride (19 mg, 28 µmol, 0.03 equiv.) and copper (I)iodide (5 mg, 28 µmol, 0.03 equiv.) were added under nitrogen and the mixture was heated to 70° C. TBAF 1M in THF (970 µl, 0.97 mmol, 1.05 equiv.) was added dropwise over a period of 20 minutes at 70° C. The reaction mixture was stirred for 2 hours at 70° C. and evaporated in presence of Isolute® sorbent to dryness. The crude product was purified by flash chromatography with a 20 g silica gel column eluting with heptane:ethyl acetate 100:0→0:100. The desired 5-(2-chloro-pyridin-4-ylethynyl)-pyridine-2-carboxylic acid tert-butylamide (210 mg, 73% yield) was obtained as a white solid, MS: m/e=314.4/316.4 (M+H$^+$).

Step 3: 5-(2-Chloro-pyridin-4-ylethynyl)-pyridine-2-carboxylic acid tert-butyl-methyl-amide

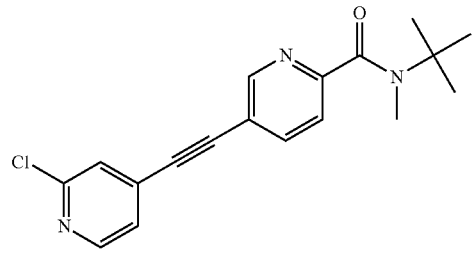 [SMILES: CN(C(=O)c1ccc(C#Cc2ccnc(Cl)c2)cn1)C(C)(C)C]

(180 mg, 574 µmol) 5-(2-Chloro-pyridin-4-ylethynyl)-pyridine-2-carboxylic acid tert-butylamide (Example 1, step 2) was dissolved in DMF (3 ml) and cooled to 0-5° C. Iodomethane (54 µl, 860 µmol, 1.5 equiv.) and NaH (55%) (41 mg, 860 µmol, 1.5 equiv.) were added and the mixture was stirred for 2 hours without cooling bath. The reaction mixture was treated with sat. NaHCO$_3$ solution and extracted twice with EtOAc. The organic layers were extracted with water, dried over sodium sulfate and evaporated to dryness. The crude product was purified by flash chromatography on silica gel (20 g, ethyl acetate/heptane gradient, 0:100 to 100:0). The desired 5-(2-chloro-pyridin-4-ylethynyl)-pyridine-2-carboxylic acid tert-butyl-methyl-amide (78 mg, 42% yield) was obtained as a yellow solid, MS: m/e=328.4/330.4 (M+H$^+$).

EXAMPLE 2

5-(3-Chloro-phenylethynyl)-pyridine-2-carboxylic acid tert-butyl-methyl-amide

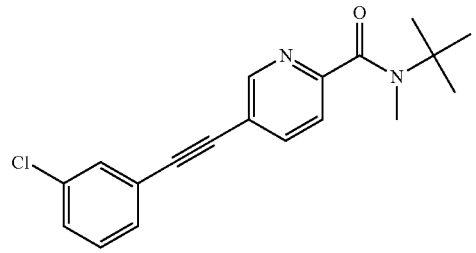

Step 1: 5-Bromo-pyridine-2-carboxylic acid tert-butyl-methyl-amide

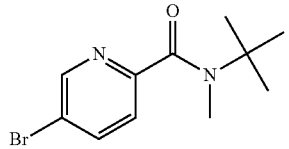

The title compound was obtained as a white solid, MS: m/e=271.2/273.2 (M+H$^+$), using chemistry similar to that described in Example 1, step 3 from 5-bromo-pyridine-2-carboxylic acid tert-butylamide (Example 1, step 1) and iodomethane.

Step 2: 5-Trimethylsilanylethynyl-pyridine-2-carboxylic acid tert-butyl-methyl-amide

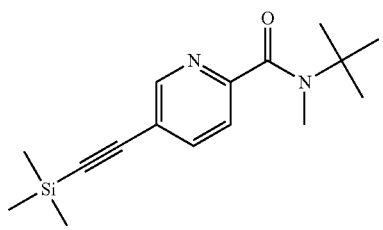 [SMILES: CN(C(=O)c1ccc(C#C[Si](C)(C)C)cn1)C(C)(C)C]

The title compound was obtained as a yellow solid, MS: m/e=289.2 (M+H$^+$), using chemistry similar to that described in Example 1, step 2 without the use of TBAF from 5-bromo-pyridine-2-carboxylic acid tert-butyl-methyl-amide (Example 2, step 1) and ethynyltrimethylsilane.

Step 3: 5-(3-Chloro-phenylethynyl)-pyridine-2-carboxylic acid tert-butyl-methyl-amide

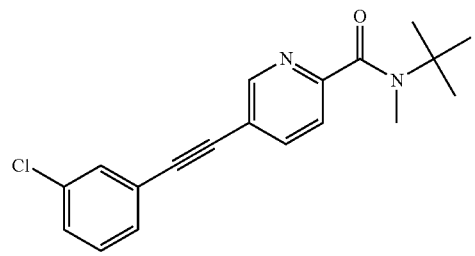

The title compound was obtained as a light yellow oil, MS: m/e=327.3/329.3 (M+H$^+$), using chemistry similar to that described in Example 1, step 2 from 5-trimethylsilanylethynyl-pyridine-2-carboxylic acid tert-butyl-methyl-amide (Example 2, step 2) and 1-chloro-3-iodobenzene.

The invention claimed is:
1. A compound of formula I
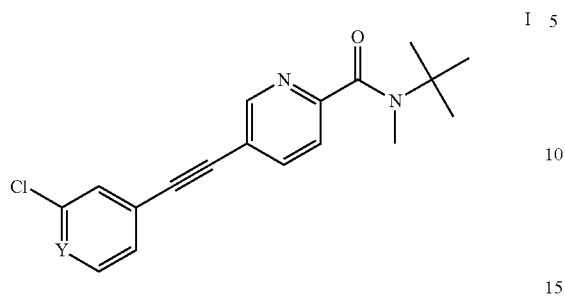
wherein
Y is CH
or a pharmaceutically acceptable acid addition salt, a racemic mixture, or its corresponding enantiomer and/or optical isomer and/or stereoisomer thereof.
2. A pharmaceutical composition comprising a compound of claim 1 and a therapeutically active carrier.
* * * * *